United States Patent [19]
Jung

[11] Patent Number: 6,153,785
[45] Date of Patent: Nov. 28, 2000

[54] 8-ALKYL-8-TRICYCLODECANYL 5-NORBORNENE-2-CARBOXYLATES AND METHOD OF PRODUCING THE SAME

[75] Inventor: Hyun-jin Jung, Seoul, Rep. of Korea

[73] Assignee: Chem Search Corp., Seoul, Rep. of Korea

[21] Appl. No.: 09/516,613

[22] Filed: Mar. 1, 2000

[30] Foreign Application Priority Data

Feb. 19, 2000 [KR] Rep. of Korea .................. 00-8033

[51] Int. Cl.$^7$ .................................................. C07C 69/74
[52] U.S. Cl. ............................................................ 560/120
[58] Field of Search ............................................ 560/120

[56] References Cited

U.S. PATENT DOCUMENTS 4,591,626  5/1986  Kawai et al. .

FOREIGN PATENT DOCUMENTS 317262  5/1989  European Pat. Off. .

OTHER PUBLICATIONS

Suwa et al, "ArF Single Layer Photoresists Based on Alkaline–Developable ROMP–H Resin," in Advances in Resist Technology and Processing XV, Will Conley, ed., Proceedings of SPIE vol. 3333, pp. 26–31, 1998.

*Primary Examiner*—Gary Geist
*Assistant Examiner*—D Khare
*Attorney, Agent, or Firm*—Reed Smith Hazel & Thomas LLP

[57] ABSTRACT

A novel norbornene carboxylate compound and a method of producing the same are provided. The norbornene carboxylate compound is 8-alkyl-8-tricyclodecanyl 5-norbornene-2-carboxylate represented by formula (1):

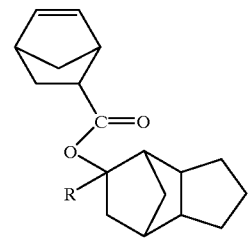

wherein R is methyl or ethyl.

4 Claims, 2 Drawing Sheets

8-ALKYL-8-TRICYCLODECANYL 5-NORBORNENE-2-CARBOXYLATES AND METHOD OF PRODUCING THE SAME

BACKGROUND OF THE INVENTION

1. Field of the Invention

The present invention relates to a novel norbornene carboxylate compound and a method of producing the same, and more particularly, to 8-alkyl-8-tricyclodecanyl 5-norbornene-2-carboxylates and a method of producing the same.

2. Description of the Related Art

Norbornene, which is a common name for bicyclo[2.2.1]-2-heptene, is an alicyclic hydrocarbon compound and is widely used in various chemical reactions due to high reactivity of cyclo-double bonds. Specifically, in a norbornene carboxylate compound having a carboxyl group introduced to norbornene, the norbornene can be easily replaced by a bulky substituent. In particular, a bulky substituent containing an alicyclic compound which has low chemical reactivity is in wide use commercially.

Norbornene compounds having a bulky alicylic substitute are commercially used as various flame retardants. Furthermore, the norbornene compound having a bulky alicyclic substituent is capable of copolymerizing with existing monomers to then be used as a polymer flame retardant. Thus, much attention is being paid to the production of norbornene compounds having a bulky alicyclic substitutent.

However, conventional norbornene carboxylate compounds having a bulky alicyclic substitutent are cumbersome in view of reaction conditions, resulting in poor yield, and the purification thereof is difficult. Thus, it is quite difficult to produce the conventional norbornene carboxylate compounds on a commercial scale.

SUMMARY OF THE INVENTION

To solve the above problems, it is an object of the present invention to provide a norbornene carboxylate compound which can be produced and purified by a simplified process to be suitable for commercial-scale production.

It is another object of the present invention to provide a method for producing the norbornene carboxylate compound.

Accordingly, to achieve the first object, there is provided 8-alkyl-8-tricyclodecanyl 5-norbornene-2-carboxylate represented by formula (1):

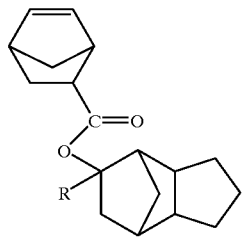

wherein R is methyl or ethyl.

To achieve the second objective, there is provided a method of producing the compound recited in claim 1, including the steps of a) synthesizing 8-alkyl-8-tricyclodecanol by reacting tricyclodecan-8-one with either an alkyl Grignard reagent or an alkyl lithium reagent, b) synthesizing 8-alkyl-8-tricyclodecanyl acrylate by reacting the 8-alkyl-8-tricyclodecanol synthesized in the step a) with acryloyl chloride, and c) applying the 8-alkyl-8-tricyclodecanyl acrylate synthesized in the step b) and cyclopentadiene to Diels-Alder reaction.

In the step (a), the alkyl group is preferably methyl or ethyl.

Preferably, the Grignard reagent is either alkyl magnesium bromide or alkyl magnesium chloride.

In the production method of the norbornene compound according to the present invention, a separation process may be performed after each step is completed. However, the separation process may be performed after all steps are performed in situ.

BRIEF DESCRIPTION OF THE DRAWINGS

The above objects and advantages of the present invention will become more apparent by describing in detail a preferred embodiment thereof with reference to the attached drawings in which.

DESCRIPTION OF THE PREFERRED EMBODIMENTS

Figure 1:
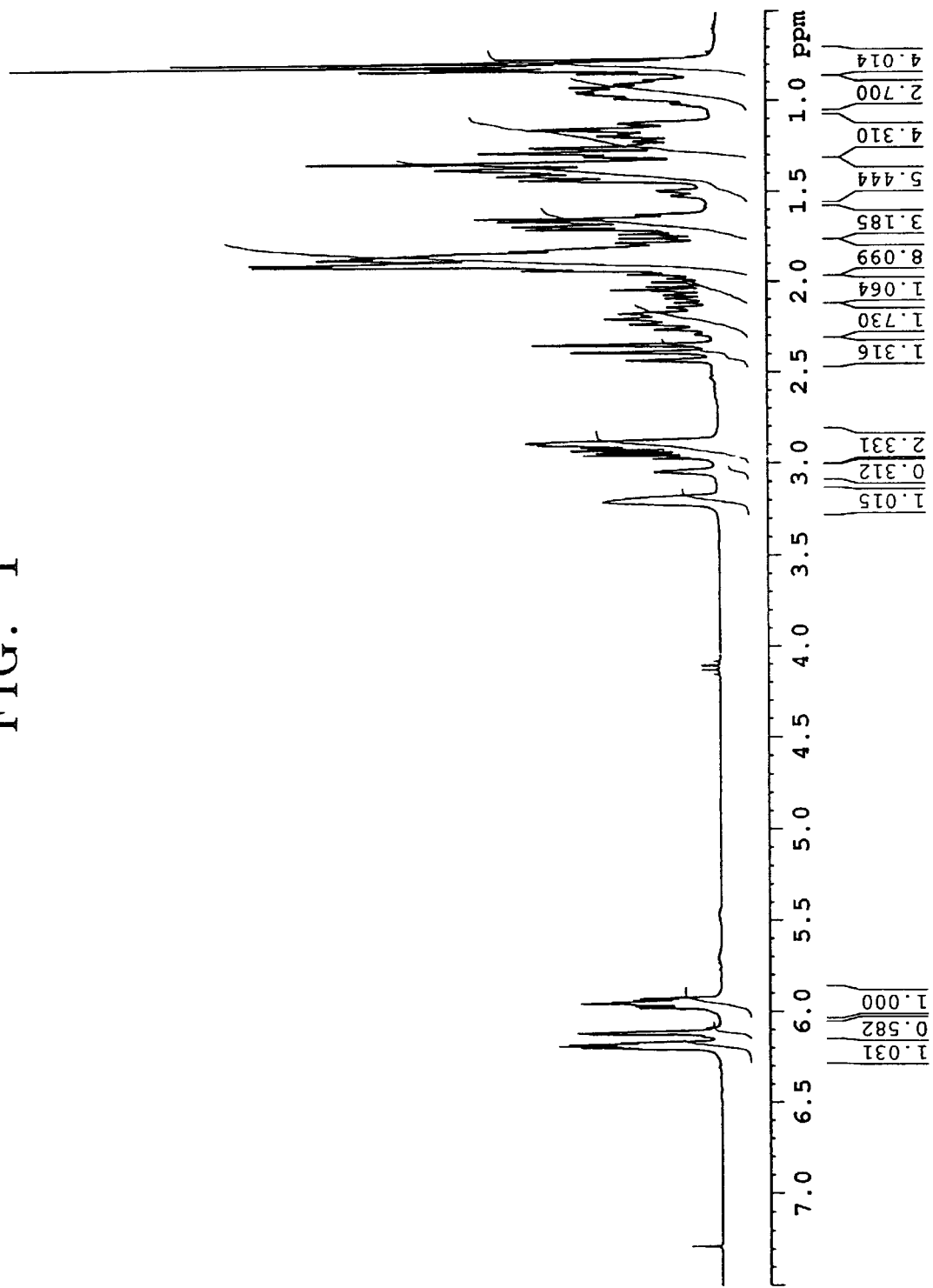
FIG. 1 is an NMR spectrum of 8-ethyl-8-tricyclodecanyl 5-norbornene-2-carboxylate produced in Example 1 of the present invention.

A process for producing 8-alkyl-8-tricyclodecanyl 5-norbornene-2-carboxylate according to the present invention will now be described in detail.

As shown in the following reaction scheme (1), tricyclodecan-8-one and an alkyl Grignard reagent or an alkyl lithium reagent are reacted to induce an alkyl group to a 8-position of tricyclodecan-8-one, thereby synthesizing 8-ethyl-8-tricyclodecanol.

Reaction Scheme (1)

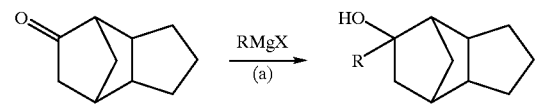

wherein R is methyl or ethyl, and X is Cl or Br.

In view of side reaction inhibition and reaction yield, if 8-ethyl-8-tricyclodecanyl 5-norbornene-2-carboxylate is a desired compound, ethyl magnesium bromide or ethyl magnesium chloride is preferably used as a Grignard reagent.

Since the above-described reaction is carried out by a general Grignard reaction mechanism, the reaction temperature and pressure are meaningless in the present invention.

Next, as shown in the following reaction scheme (2), 8-alkyl-8-tricyclodecanol and acryloyl chloride are reacted to synthesize 8-alkyl-8-tricyclodecanyl acrylate.

Reaction Scheme (2)

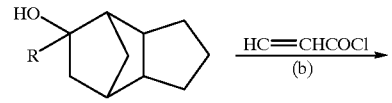

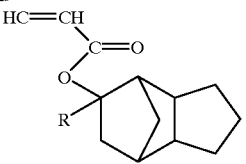

Finally, as shown in the following reaction scheme (3), a norbornene substitute is prepared by the Diels-Alder reaction of 8-alkyl-8-tricyclodecanyl acrylate and cyclopentadiene, thereby obtaining 8-alkyl-8-tricyclodecanyl 5-norbornene-2-carboxylate.

Reaction Scheme (3)

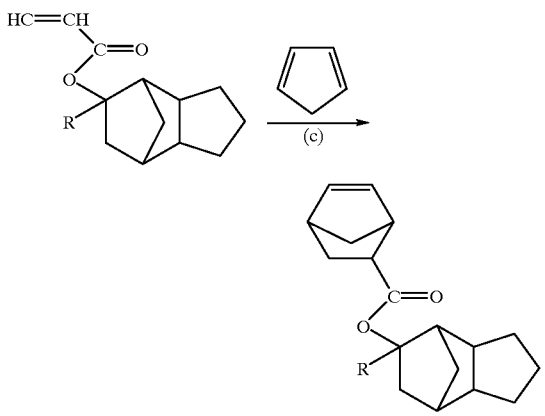

The present invention is described in more detail below by referring to the following examples, and the examples are intended to illustrate but not limit the invention.

EXAMPLE 1

8-ethyl-8-tricyclodecanyl 5-norbornene-2-carboxylate a. Synthesis of 8-ethyl-8-tricyclodecanol 440 ml of a solution of ethyl magnesium bromide (1.0 M) in tetrahydrofuran (THF) was diluted with 100 ml of anhydrous THF. Then, the solution was put into a 1 liter flask and then maintained at 0° C. Tricyclodecan-8-one (60 g, 0.4 mol) was dropped slowly using a dropping funnel and then the reaction was stirred at room temperature for about 12 hours. After completion of the reaction, excess THF was removed using a rotary evaporator and then the resultant product was poured into water. Then, the resultant product was neutralized with dilute sulfuric acid and extracted using diethyl ether and was then dried over magnesium sulfate. The obtained crude product was filtered by column chromatography (n-hexane:ethylacetate=8:1) to yield the desired product 8-ethyl-8-tricyclodecanol (yield: 70%).

b. Synthesis of 8-ethyl-8-tricyclodecanyl acrylate 8-ethyl-8-tricyclodecanol (36 g, 0.2 mol) and triethylamine (0.22 mol) were dissolved in 250 ml of THF and then acryloyl chloride (19 g, 0.21 mol) was added slowly thereto using a dropping funnel. Then, the reaction was stirred at room temperature for about 12 hours. After completion of the reaction, excess THF was removed using a rotary evaporator and then the resultant product was poured into water. Then, the resultant product was neutralized with dilute chloric acid and extracted using diethyl ether and was then dried over magnesium sulfate. The obtained crude product was filtered by column chromatography (n-hexane:ethylacetate=4:1) to yield the desired product 8-ethyl-8-tricyclodecanyl acrylate (yield: 80%).

$^1$H-NMR (CDCl$_3$; ppm): 6.3 (1H, d), 6.1 (1H, dd), 5.7 (1H, d), 2.5 (1H, s), 2.2 (2H, m), 1.4 (2H, d), 0.8 (3H, t).

Figure 2:
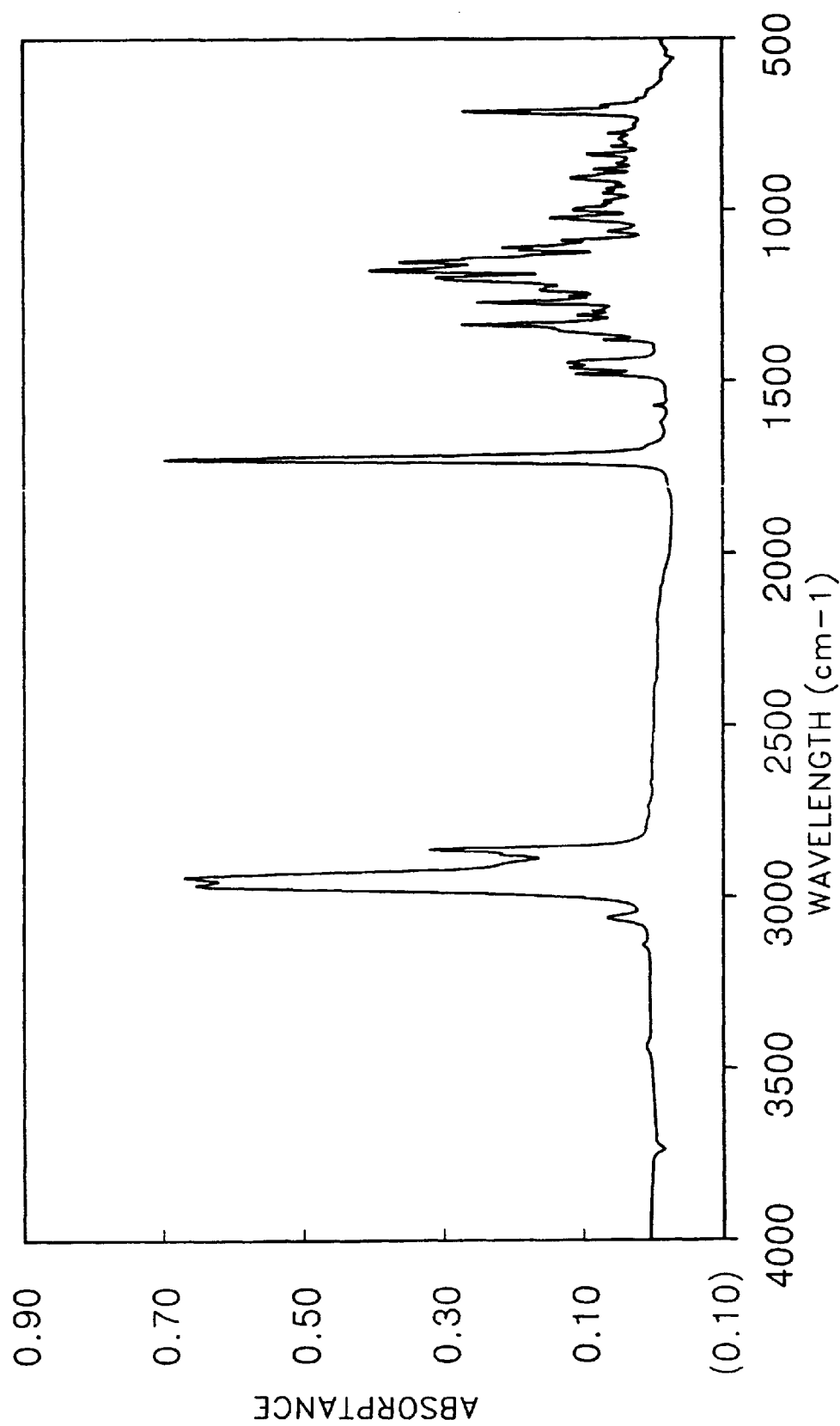
FIG. 2 is an FT-IR spectrum of 8-ethyl-8-tricyclodecanyl 5-norbornene-2-carboxylate produced in Example 1 of the present invention.

FT-IR (NaCl; cm$^{-1}$): 2947, 2863, 1722, 1638, 1621, 1402, 1205 c. Synthesis of 8-ethyl-8-tricyclodecanyl 5-norbornene-2-carboxylate 8-ethyl-8-tricyclodecanyl acrylate (47 g, 0.2 mol) was dissolved in 250 ml of THF, cyclopentadiene (20 g, 0.3 mol) was added slowly thereto at 0° C. and then the reaction temperature was raised to about 50° C. Then, the reaction was stirred for about 20 hours. After completion of the reaction, excess THF was removed using a rotary evaporator and then the crude product was vacuum-distilled to yield the desired compound of viscous colorless liquid (yield: 90%) FIGS. 1 and 2 are NMR and FT-IR spectrums of the compound.

$^1$H-NMR (CDCl$_3$; ppm): 6.2 (1H, m), 6.1 (1H, s), 5.9 (1H, m), 3.2 (1H, s), 2.9 (2H, m), 2.4–0.8 (m).

FT-IR (NaCl; cm$^{-1}$): 2944, 2863, 1727, 1335, 1270, 1177, 712

EXAMPLE 2

8-methyl-8-tricyclodecanyl 5-norbornene-2-carboxylate

The title compound was prepared in the same manner as in Example 1, except that 3.0 M diethyl ether solution of methyl magnesium bromide was used instead of 1.0 M THF solution of ethyl magnesium chloride (yield: 70%).

8-alkyl-8-tricyclodecanyl 5-norbornene-2-carboxylate according to the present invention can be produced in a high yield by a simple process and is advantageous for mass production of a commercial scale. A norbornene compound having a bulky substituent can be commercially used as various kinds of flame retardants and is capable of copolymerizing with existing monomers to be used as polymer flame retardants. Further, the norbornene compound can be useful in various applications which require the intrinsic reactivity of norbornene itself.

What is claimed is:

1. 8-alkyl-8-tricyclodecanyl 5-norbornene-2-carboxylate represented by formula (1):

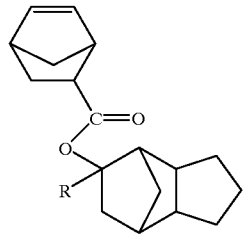

wherein R is methyl or ethyl.

2. A method of producing the compound recited in claim 1, comprising the steps of:
   a) synthesizing 8-alkyl-8-tricyclodecanol by reacting tricyclodecan-8-one with either an alkyl Grignard reagent or an alkyl lithium reagent;
   b) synthesizing 8-alkyl-8-tricyclodecanyl acrylate by reacting the 8-alkyl-8-tricyclodecanol synthesized in the step a) with acryloyl chloride; and c) applying the 8-alkyl-8-tricyclodecanyl acrylate synthesized in the step b) and cyclopentadiene to Diels-Alder reaction.

3. The method according to claim 2, wherein the Grignard reagent is either alkyl magnesium bromide or alkyl magnesium chloride.

4. The method according to claim 2, wherein if the alkyl is ethyl, ethyl magnesium bromide or ethyl magnesium chloride is used as the Grignard reagent.

* * * * *